(12) United States Patent
Lim et al.

US009592323B2

(10) Patent No.: US 9,592,323 B2
(45) Date of Patent: Mar. 14, 2017

(54) COATING COMPRISING AN AMORPHOUS PRIMER LAYER AND A SEMI-CRYSTALLINE RESERVOIR LAYER

(71) Applicant: ABBOTT CARDIOVASCULAR SYSTEMS INC., Santa Clara, CA (US)

(72) Inventors: Florencia Lim, Union City, CA (US); Mikael O. Trollsas, San Jose, CA (US); Syed F.A. Hossainy, Hayward, CA (US); Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/109,795

(22) Filed: Dec. 17, 2013

(65) Prior Publication Data
US 2014/0178454 A1    Jun. 26, 2014

Related U.S. Application Data

(63) Continuation of application No. 12/124,991, filed on May 21, 2008, now Pat. No. 8,661,630.

(51) Int. Cl.
*A61L 31/10* (2006.01)
*A61L 31/16* (2006.01)
*A61L 31/14* (2006.01)

(52) U.S. Cl.
CPC ............. *A61L 31/10* (2013.01); *A61L 31/148* (2013.01); *A61L 31/16* (2013.01); *A61L 2300/604* (2013.01); *A61L 2300/606* (2013.01); *Y10T 24/258* (2015.01)

(58) Field of Classification Search
None
See application file for complete search history.

(56) References Cited

U.S. PATENT DOCUMENTS

| | | | |
|---|---|---|---|
| 4,885,171 A | 12/1989 | Surendra et al. | |
| 5,076,807 A | 12/1991 | Bezwada et al. | |
| 5,085,628 A | 2/1992 | Engebretson et al. | |
| 5,085,629 A | 2/1992 | Goldberg et al. | |
| 5,442,032 A | 8/1995 | Arnold et al. | |
| 5,605,696 A | 2/1997 | Eury et al. | |
| 5,631,015 A | 5/1997 | Bezwada et al. | |
| 5,649,977 A | 7/1997 | Campbell | |
| 5,653,992 A | 8/1997 | Bezwada et al. | |
| 5,670,161 A | 9/1997 | Healy et al. | |
| 5,733,327 A | 3/1998 | Igaki et al. | |
| 5,824,048 A | 10/1998 | Tuch | |
| 5,834,582 A * | 11/1998 | Sinclair et al. ............... | 528/354 |
| 5,971,987 A | 10/1999 | Huxel et al. | |
| 6,143,037 A | 11/2000 | Goldstein et al. | |
| 6,153,252 A | 11/2000 | Hossiany et al. | |
| 6,156,373 A | 12/2000 | Zhong et al. | |
| 6,165,202 A | 12/2000 | Kokish et al. | |
| 6,239,124 B1 | 5/2001 | Zenke et al. | |
| 6,368,658 B1 | 4/2002 | Schwarz et al. | |
| 6,939,376 B2 | 9/2005 | Shulze et al. | |
| 7,682,387 B2 | 3/2010 | Shulze et al. | |
| 7,727,275 B2 | 6/2010 | Betts et al. | |
| 8,252,046 B2 | 8/2012 | Shulze et al. | |
| 8,308,795 B2 | 11/2012 | Shulze et al. | |
| 8,481,651 B2 | 7/2013 | Hissink et al. | |
| 8,545,550 B2 | 10/2013 | Shulze et al. | |
| 8,661,630 B2 | 3/2014 | Lim et al. | |
| 8,697,113 B2 | 4/2014 | Lim et al. | |
| 8,715,341 B2 | 5/2014 | Shulze et al. | |
| 2002/0016625 A1 | 2/2002 | Falotico et al. | |
| 2003/0125800 A1 | 7/2003 | Shulze et al. | |
| 2003/0219562 A1 | 11/2003 | Rypacek et al. | |
| 2005/0079202 A1 | 4/2005 | Chen et al. | |
| 2005/0112171 A1 | 5/2005 | Tang et al. | |
| 2005/0233062 A1* | 10/2005 | Hossainy et al. ............... | 427/2.1 |
| 2005/0287184 A1 | 12/2005 | Hossainy et al. | |
| 2006/0062821 A1 | 3/2006 | Simhambhatla et al. | |
| 2006/0088571 A1* | 4/2006 | Chen et al. .................. | 424/426 |
| 2006/0135943 A1 | 6/2006 | Mandrusov et al. | |
| 2006/0246109 A1 | 11/2006 | Hossainy et al. | |
| 2007/0134305 A1 | 6/2007 | Zilberman | |
| 2007/0141112 A1 | 6/2007 | Falotico et al. | |
| 2007/0149640 A1* | 6/2007 | Andjelic et al. ............... | 523/105 |
| 2007/0196423 A1* | 8/2007 | Ruane et al. .................. | 424/423 |
| 2007/0202046 A1 | 8/2007 | Dave | |
| 2007/0224244 A1 | 9/2007 | Weber et al. | |
| 2007/0264307 A1 | 11/2007 | Chen et al. | |
| 2007/0299510 A1* | 12/2007 | Venkatraman et al. ..... | 623/1.44 |

(Continued)

FOREIGN PATENT DOCUMENTS

EP    1 112 724 A2    12/2000
EP     112 724 A2  * 12/2000

(Continued)

OTHER PUBLICATIONS

U.S. Appl. No. 11/872,393, filed Oct. 10, 2007, Kleiner et al.
U.S. Appl. No. 11/870,394, filed Oct. 10, 2007, Kleiner et al.
Notice of Reasons for Rejection from JPO, dated May 27, 2014, for Appl. No. JP2012-510857, 3 pgs.
The translation of the Notice of Reason for Rejection from JPO, dated May 27, 2014, for Appl. No. JP2012-510882, 3 pgs.
Bagheri et al. "Synthesis and Characterication of Biodegradable Random Copolymers of L-Lactide, Glycolide and Trimethylene Carbonate", Iranian Polymer Journal 16: pp. 489-494 (2007).

(Continued)

*Primary Examiner* — Robert A Wax
*Assistant Examiner* — Danah Al-Awadi
(74) *Attorney, Agent, or Firm* — Squire Patton Boggs (US) LLP

(57) ABSTRACT

The present invention provides a coating comprising a reservoir layer comprising a semi-crystalline polymer and a primer layer comprising an amorphous polymer on an implantable device and methods of making and using the same.

20 Claims, 3 Drawing Sheets

(56) References Cited

U.S. PATENT DOCUMENTS

| | | | |
|---|---|---|---|
| 2008/0008735 A1 | 1/2008 | Diener |
| 2008/0091262 A1 | 4/2008 | Gale et al. |
| 2008/0103584 A1 | 5/2008 | Su et al. |
| 2009/0004243 A1 | 1/2009 | Pacetti et al. |
| 2009/0104241 A1 | 4/2009 | Pacetti et al. |
| 2009/0110713 A1 | 4/2009 | Lim et al. |
| 2009/0111787 A1 | 4/2009 | Lim et al. |
| 2009/0263457 A1 | 10/2009 | Trollsas et al. |
| 2009/0285873 A1 | 11/2009 | Lim et al. |
| 2009/0297584 A1 | 12/2009 | Lim et al. |
| 2009/0306120 A1 | 12/2009 | Lim et al. |
| 2014/0107592 A1 | 4/2014 | Lim et al. |

FOREIGN PATENT DOCUMENTS

| | | | |
|---|---|---|---|
| EP | 1 505 930 A | | 2/2005 |
| EP | 1 518 517 A2 | | 3/2005 |
| EP | 1 764 118 | | 3/2007 |
| EP | 2 113 230 A2 | | 11/2009 |
| EP | 2 417 943 A1 | | 2/2012 |
| EP | 2 578 186 A2 | | 4/2013 |
| JP | 3-205059 | | 9/1991 |
| JP | 2005-516736 T | | 6/2005 |
| JP | 2007-190369 A | | 8/2007 |
| JP | 2007-521069 T | | 8/2007 |
| WO | WO 97/35575 A1 | | 10/1997 |
| WO | WO 00/50007 A1 | | 8/2000 |
| WO | WO 01/87368 A1 | | 11/2001 |
| WO | WO 02/07601 A2 | | 1/2002 |
| WO | WO 02/18477 A2 | | 3/2002 |
| WO | WO 02/47731 A2 | | 6/2002 |
| WO | WO 03/068289 | | 8/2003 |
| WO | WO 03/082368 A1 | | 10/2003 |
| WO | WO 03/090818 A2 | | 11/2003 |
| WO | WO 2004/091680 | | 10/2004 |
| WO | WO 2005/004945 | | 1/2005 |
| WO | WO 2005/047295 A1 | | 5/2005 |
| WO | WO 2005/068533 | | 7/2005 |
| WO | WO 2006/065685 | | 6/2006 |
| WO | WO 2007/009919 A2 | | 1/2007 |
| WO | WO 2007/121019 | | 10/2007 |
| WO | WO 2009/036083 | | 3/2009 |
| WO | WO 2009/055426 | | 4/2009 |
| WO | WO 2009/058666 | | 5/2009 |

OTHER PUBLICATIONS

Cai et al., "Relationship Among Drug Delivery Behavior, Degradation Behavior and Morpology of Copolylactones Derived from Glycolide, L-Lactide and ϵ—Caprolactone", Polymers for Advanced Technologies 13, pp. 105-111 (2002).
Cai et al., "Synthesis and Characterization of Polycaprolactone (B)-Poly(lactide-co-glycolide) (A) ABA Block Copolymer", Polymers for Advanced Technologies, 11, pp. 159-166 (2000).
Channuan et al. "Investigation of the Crystal Structure in Segmented Triblock L-Lactide, ϵ-Caprolactone and Glycolide Terpolymer Fibers". Chian Mai J. Sci. 32(3): (2005) Abstract 1 pg.
Choi et al. "Synthesis and characterization of elastic PLGA/PCL/PLGA tri-block copolymers", J. Biomater. Sci. Polymer Edn, vol. 13, No. 10 pp. 1163-1173 (2002).
Drachman et al., *Neointimal Thickening After Stent Delivery of Paclitaxel: Change in Composition and Arrest of Growth Over Six Months*, J. of the American College of Cardiology vol. 36, No. 7, pp. 2325-2332 (2000).
Harper Drug Latentiation, Progress in Drug Research vol. 4, pp. 257-294 (1962).
Hori et al., "Ring-Opening Polymerization of Optically Active β-Butyrolactone Using Distannoxane Catalysts: Synthesis of High Molecular Weight Poly(3 hydroxybutyrate)", Macromolecules 26, pp. 5533-5534 (1993).
Kasperczyk, *Microstructural analysis of poly*[(L,L-lactide)-*co* -(glycolide)] *by$^1$H and $^{13}$C n.m.r. spectroscopy*, Polymer 37(2), pp. 201-203 (1996).
Koleske et al. "Lactone Polymers. I. Glass Transition Temperature of Poly-ϵ-caprolactone by Means of Compatible Polymer Mixtures", Journal of Polymer Science 7, pp. 795-807 (1969).
Lee et al., *Elastic biodegradable poly*(glycolide-co-caprolactone) *scaffold for tissue engineering*, J. Biomed. Mater. Res. A, 66 pp. 29-37 Abstract 1 pg. (2003).
Mangkorn Srisa-ard et al. *Synthesis and characterization of a random terpolymer of L-lactide, ϵ-caprolactone and glycolide*, Polym. Int. 50 (8) pp. 891-896 (2001).
Martin et al., *Enhancing the biological activity of immobilized osteopontin using a type-1 collagen affinity coating*, J. Biomed. Mater. Res. 70A, pp. 10-19 (2004).
Matyjaszewski, Handbook of Radical Polymerization, Ed. John Willey & Sons, p. 789 (2002).
MSDS, Safety data for dl-beta-hydroxybutyric acid lactone 2 pgs. (2004).
Pamula et al., "Hydrolytic degradation of porous scaffolds for tissue engineering from terpolymer of L-lactide, ϵ-caprolactone and glycolide", Journal of Molecular Structure pp. 744-747 and 557-562 (2005).
Raval et al., "Novel Biodegradable polymeric Matrix Coated Cardiovascular Stent for Controlled Drug Delivery", Trends Biomater. Artif. Organs, vol. 20(2), pp. 131-141 (2007).
Sawhney et al., "Rapdly degraded terpolymers of dl-lactide, glycolide and e-caprolactone with increased hydrophilicity by copolymerization with polyethers", Journal of Biomedical Materials Research, vol. 24, pp. 1397-1411 (1990).
Serruys et al., *A Randomized Comparison of the Value of Additional Stenting After Optimal Balloon Angioplasty for Long Coronary Lesions*, J. of Am. College of Cardiology vol. 39, No. 3, pp. 393-399 (2002).
Sinkula et al., *Rationale for Design of Biologically Reversible Drug Derivatives: Prodrugs*, J. of Pharmac. Science vol. 64, No. 2, pp. 181-210 (1975).
Spagnuolo et al., *Gas1 as induced by VE-cadherin and vascular endothelial growth factor and inhibits endothelial cell apoptosis*, Blood vol. 103, No. 8, pp. 3005-3012 (2004).
Stella et al., *Prodrugs Do They Have Advantages in Clinical Practice?*, Drugs 29, pp. 455-473 (1985).
Tollon Fabrication of Coated Biodegradable Polymer Scaffolds and Their Effects on Murine Embryonic Stem Cells, University of Florida, pp. 1-5 (2005).
Völkel et al., *Targeting of immunoliposomes to endothelial cells using a single—chain Fv fragment directed against human endoglin (CD105)*, Biochemica et Biophysica Acta, vol. 1663, pp. 158-166 (2004).
Waksman "Biodegradable Stents: They do their job and disappear" Journal of Invasive Cardiology, vol. 18, issue 2, pp. 1-8 (2006).
International Search Report and Written Opinion of PCT/US2008/080719 filed Oct. 22, 2009, mailed Jan. 15, 2010.
International Search Report and Written Opinion of PCT/US2009/043379 filed May 8, 2009, mailed Jul. 20, 2010.
International Search Report and Written Opinion of PCT/US2010/033591 filed May 4, 2010, mailed Sep. 9, 2010.
International Search Report and Written Opinion of PCT/US2010/033787 filed May 5, 2010, mailed Feb. 3, 2011.
Pêgo, Ap et al. "In vivo behavior of poly(1,3-trimethylene carbonate) and copolymers of 1,3-trimethylene carbonate with D,L-lactide or epsilon-caprolactone: Degredation and tissue response," Biomed Mater Res A., Dec. 1, 2003, vol. 67(3), pp. 1044-1054, Abstract only, 1 pp.
Guidant Press Releases Mar. 27, 2002 Guidant licenses Everolimus from Novartis for Drug Eluting Stents, *Boston Scientific*, Jun. 23, 2015, pp. 1-3.
Jain, "The manufacturing techniques of carious drug loaded biodegradable poly(lactide-co-glycolide)(PLGA) devices," *Biomaterials*, 2000, vol. 21, Issue 23, pp. 2475-2490.

\* cited by examiner

COATING COMPRISING AN AMORPHOUS PRIMER LAYER AND A SEMI-CRYSTALLINE RESERVOIR LAYER

CROSS-REFERENCE TO RELATED APPLICATIONS

This application is a continuation of U.S. application Ser. No. 12/124,991, filed on May 21, 2008, and published as U.S. Patent Application Publication Number 2009-0291111 A1 on Nov. 26, 2009, which is incorporated by reference herein in its entirety, including any drawings, and is incorporated by reference for all purposes.

FIELD OF THE INVENTION

The present invention relates to a semi-crystalline composition for coating an implantable device.

BACKGROUND OF THE INVENTION

Percutaneous coronary intervention (PCI) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the blood conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of the arterial lining and to reduce the chance of thrombosis or restenosis, a stent is implanted in the artery to keep the artery open.

Drug delivery stents have reduced the incidence of in-stent restenosis (ISR) after PCI (see, e.g., Serruys, P. W., et al., J. Am. Coll. Cardiol. 39:393-399 (2002)), which has plagued interventional cardiology for more than a decade. However, a few challenges remain in the art of drug delivery stents. For example, compromised coating integrity when an amorphous bioabsorbable polymer is used for coating a stent, which can result from the conditions of ethylene oxide (ETO) sterilization or from the conditions of crimping a stent onto the delivery balloon. Conditions such as elevated temperature, high relative humidity, and high concentration of ETO in the ETO sterilization process can result in plasticization and adhesion of the coating to the balloon via polymer deformation and flow. In a similar way a completely amorphous bioabsorbable polymer may flow when crimped at elevated temperatures on to the delivery balloon.

The embodiments of the present invention address the above-identified needs and issues.

SUMMARY OF THE INVENTION

The present invention provides a medical device comprising a coating that comprises a layer comprising a semi-crystalline polymer and a primer layer comprising an amorphous polymer. The semi-crystalline polymer comprises one or more crystalline domains and one or more amorphous domains. In addition, the crystalline domains have melting temperature ($T_m$s) and a mass ratio to (of 10 to 30%) the amorphous domains so as to prevent a coating formed of the semi-crystalline polymer from flowing or adhering to a balloon used with the medical device in a process forming or treating the coating, e.g., ETO sterilization at a temperature above or around the glass transition temperature of the drug containing polymer and/or a stent crimping process at temperatures above or around the glass transition temperature of the drug containing polymer. The primer layer comprising an amorphous polyester polymer generally has good adhesion to the metallic substrate of an implantable device and degrades faster than the semi-crystalline polyester polymer.

Therefore, a coating including these layers has improved coating integrity while maintaining mechanical integrity after EtO sterilization. In addition, due the faster absorption of the amorphous polymer, the length of time for bioabsorption of a coating comprising the layer comprising the semi-crystalline polymer and a primer layer comprising an amorphous layer can be tailored by the difference of rate of absorption of the amorphous primer layer and the semi-crystalline layer. Further, a coating as described herein has better shelf-life stability and release rate reproducibility resulting from the attributes of the layer comprising the semi-crystalline polymer.

The coating described herein is generally degradable or bioabsorbable. In some embodiments, the coating can degrade within about 1 month, 2 months, 3 months, 4 months, 6 months, 12 months, 18 months, or 24 months after implantation of a medical device comprising the coating. Total degradation here implies complete loss of mass. In some embodiments, the coating can completely degrade or absorb within 24 months after implantation of a medical device comprising the coating.

In some embodiments, the coating can include one or more bioactive agents, e.g., drug(s). Some exemplary bioactive agents that can be included in a coating having a hygroscopic layer described above are paclitaxel, docetaxel, estradiol, 17-beta-estradiol, nitric oxide donors, super oxide dismutases, super oxide dismutases mimics, 4-amino-2,2,6, 6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), temsirolimus, deforolimus, γ-hiridun, clobetasol, pimecrolimus, imatinib mesylate, midostaurin, feno fibrate, prodrugs thereof, co-drugs thereof, and combinations thereof. Some other examples of the bioactive agent include siRNA and/or other oligonucleotides that inhibit endothelial cell migration. Some further examples of the bioactive agent can also be lysophosphatidic acid (LPA) or sphingosine-1-phosphate (S1P). LPA is a "bioactive" phospholipid able to generate growth factor-like activities in a wide variety of normal and malignant cell types. LPA plays an important role in normal physiological processes such as wound healing, and in vascular tone, vascular integrity, or reproduction.

The implantable device described herein can be formed on an implantable device such as a stent, which can be implanted in a patient to treat, prevent, mitigate, or reduce a vascular medical condition, or to provide a pro-healing effect. In some embodiments, the vascular medical condition or vascular condition is a coronary artery disease (CAD)

and/or a peripheral vascular disease (PVD). Some examples of such vascular medical diseases are restenosis and/or atherosclerosis. Some other examples of these conditions include thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DETAILED DESCRIPTION

Figure 1:
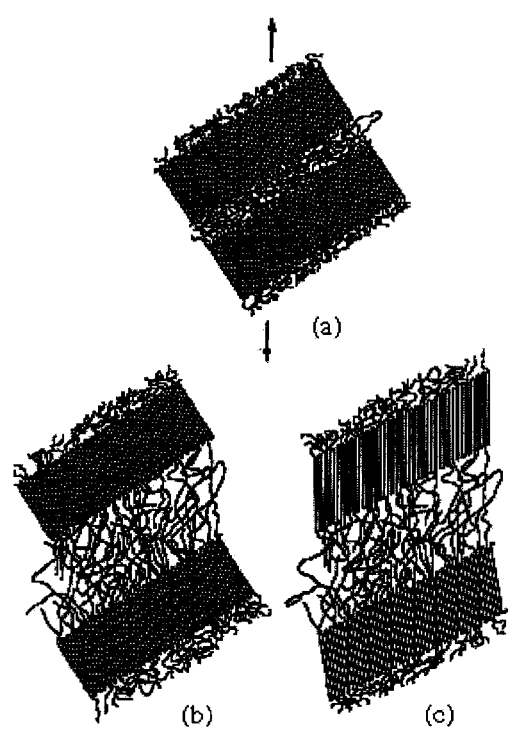
FIG. 1 illustrates a semi-crystalline polymer having crystalline domains (heavy blocks) and amorphous domains (waving lines)
Figure 2:
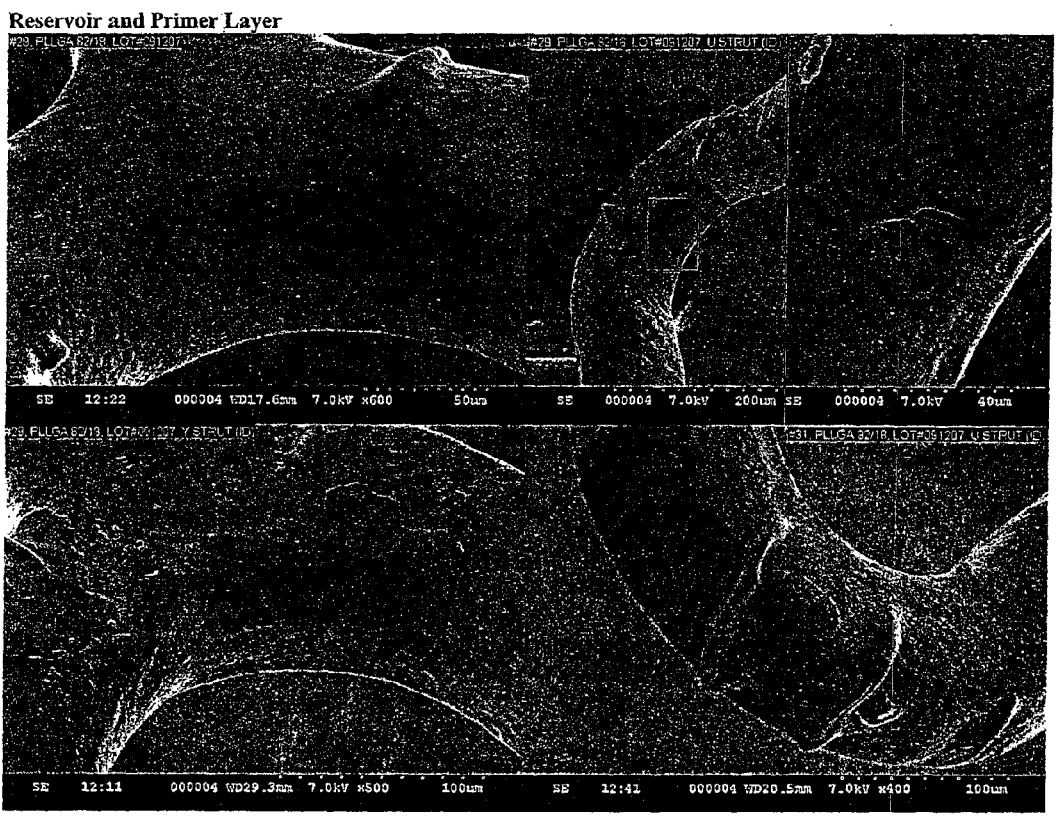
FIG. 2 shows scanning electron micrograph (SEM) images of coating integrity after simulated use for semicrystalline PLLGA (82/18) as drug reservoir and as primer layer.

The present invention provides a medical device comprising a coating that comprises a layer comprising a semi-crystalline polymer and a primer layer comprising an amorphous polymer. The semi-crystalline polymer comprises one or more crystalline domains and one or more amorphous domains. In addition, the crystalline domains have melting temperature ($T_m$s) and a mass ratio to (of 10-30%) the amorphous domains so as to prevent a coating formed of the semi-crystalline polymer from flowing or adhering to a balloon used with the medical device in a process forming or treating the coating, e.g., ETO sterilization at a temperature above or around the glass transition temperature of the drug containing polymer and/or a stent crimping process at temperatures above or around the glass transition temperature of the drug containing polymer. A primer layer comprising an amorphous polyester polymer generally has good adhesion to the metallic substrate of an implantable device and degrades faster than the semi-crystalline polyester polymer.

The amorphous polyester polymer can be selected to be partially or completely miscible with the reservoir layer such that the reservoir layer and the primer layer can have good compatibility. In some embodiments, a miscibility of at least 5%, 10%, 20%, 30%, 40%, 50%, 70%, 90%, or 95% of the primer polymer in the reservoir polymer is selected.

In some embodiments, the amorphous polymer for forming the primer layer can be selected to have a glass-transition temperature ($T_g$) lower than the $T_g$ of the reservoir polymer.

A coating including these layers has improved coating integrity while maintaining mechanical integrity after EtO sterilization. In addition, the amorphous polymer can have a rate of degradation or absorption faster or slower than the reservoir layer, and thus, the length of the time of bioabsorption of a coating comprising the layer comprising the semi-crystalline polymer and a primer layer comprising an amorphous layer can be tailored by the difference of rate of absorption of the amorphous primer layer and the semi-crystalline layer. Further, a coating as described herein has better shelf-life stability and release rate reproducibility resulting from the attributes of the layer comprising the semi-crystalline polymer.

Generally, a coating described herein can degrade or absorb at a rate that the coating will have about 80% or more mass loss within a period of 6 months after deployment (e.g., implanted in a blood vessel of a patient). In some embodiments, the coating mass loss within the same period can be about 90% or more, 95% or more, or about 99% or more.

As used herein, the term "layer comprising a semi-crystalline polymer" is used interchangeably with the term "semi-crystalline layer", and the term "primer layer comprising an amorphous polymer" is used interchangeably with the term "amorphous primer layer" or "amorphous layer". In some embodiments, the term "semi-crystalline layer" is referred to as "reservoir layer", and the term "amorphous primer layer" is sometimes referred to as "primer layer."

In some embodiments, the term "domain" can be referred to as "phase." Therefore, the term "crystalline domain" can be referred to as "crystalline phase." Similarly, the term "amorphous domain" can be referred to as "amorphous phase."

As used herein, the term "semi-crystalline copolymer" is used interchangeably with the term "semi-crystalline polymer." In some embodiments, the semi-crystalline polymer can be a copolymer formed of two or more monomers. In some embodiments, the semi-crystalline polymer can be a homopolymer formed of one monomer.

The coating described herein is generally degradable or bioabsorbable. In some embodiments, the coating can degrade within about 1 month, 2 months, 3 months, 4 months, 6 months, 12 months, 18 months, or 24 months after implantation of a medical device comprising the coating. In some embodiments, the coating can completely degrade or absorb within 24 months after implantation of a medical device comprising the coating.

In some embodiments, the coating can include one or more other biocompatible polymers, which are described below.

In some embodiments, the coating can include one or more bioactive agents, e.g., drug(s). Some exemplary bioactive agents that can be included in a coating having a hygroscopic layer described above are paclitaxel, docetaxel, estradiol, 17-beta-estradiol, nitric oxide donors, super oxide dismutases, super oxide dismutases mimics, 4-amino-2,2,6, 6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), temsirolimus, γ-hiridun, clobetasol, pimecrolimus, imatinib mesylate, midostaurin, feno fibrate, prodrugs thereof, co-drugs thereof, and combinations thereof. Some other examples of the bioactive agent include siRNA and/or other oligonucleotides that inhibit endothelial cell migration. Some further examples of the bioactive agent can also be lysophosphatidic acid (LPA) or sphingosine-1-phosphate (S1P). LPA is a "bioactive" phospholipid able to generate growth factor-like activities in a wide variety of normal and malignant cell types. LPA plays an important role in normal physiological processes such as wound healing, and in vascular tone, vascular integrity, or reproduction.

The implantable device described herein can be formed on an implantable device such as a stent, which can be implanted in a patient to treat, prevent, mitigate, or reduce a vascular medical condition, or to provide a pro-healing effect. In some embodiments, the vascular medical condition or vascular condition is a coronary artery disease (CAD) and/or a peripheral vascular disease (PVD). Some examples of such vascular medical diseases are restenosis and/or atherosclerosis. Some other examples of these conditions include thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DEFINITIONS

Wherever applicable, the definitions to some terms used throughout the description of the present invention as provided below shall apply.

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are used interchangeably and refer to polymers and coatings that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human), e.g., fragments having a molecular weight of about 40,000 Daltons (40 kDa) or less. The process of breaking down and eventual absorption and elimination of the polymer or coating can be caused by, e.g., hydrolysis, metabolic processes, oxidation, enzymatic processes, bulk or surface erosion, and the like. Conversely, a "biostable" polymer or coating refers to a polymer or coating that is not biodegradable.

Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. Whenever the terms "degradable," "biodegradable," or "biologically degradable" are used in this application, they are intended to broadly include biologically degradable, biologically erodable, biologically absorbable, and biologically resorbable polymers or coatings.

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal." In the context of a blood-contacting implantable device, a "prohealing" drug or agent refers to a drug or agent that has the property that it promotes or enhances re-endothelialization of arterial lumen to promote healing of the vascular tissue.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N. J. Harper, Drug latentiation, *Prog Drug Res.*, 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.*, 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs*, 29: 455-473 (1985).

The terms "polymer" and "polymeric" refer to compounds that are the product of a polymerization reaction. These terms are inclusive of homopolymers (i.e., polymers obtained by polymerizing one type of monomer), copolymers (i.e., polymers obtained by polymerizing two or more different types of monomers), terpolymers, etc., including random, alternating, block, graft, dendritic, crosslinked and any other variations thereof.

As used herein, the term "implantable" refers to the attribute of being implantable in a mammal (e.g., a human being or patient) that meets the mechanical, physical, chemical, biological, and pharmacological requirements of a device provided by laws and regulations of a governmental agency (e.g., the U.S. FDA) such that the device is safe and effective for use as indicated by the device. As used herein, an "implantable device" may be any suitable substrate that can be implanted in a human or non-human animal. Examples of implantable devices include, but are not limited to, self-expandable stents, balloon-expandable stents, coronary stents, peripheral stents, stent-grafts, catheters, other expandable tubular devices for various bodily lumen or orifices, grafts, vascular grafts, arterio-venous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-eluting particles, microparticles and nanoparticles). The stents may be intended for any vessel in the body, including neurological, carotid, vein graft, coronary, aortic, renal, iliac, femoral, popliteal vasculature, and urethral passages. An implantable device can be designed for the localized delivery of a therapeutic agent. A medicated implantable device may be constructed in part, e.g., by coating the device with a coating material containing a therapeutic agent. The body of the device may also contain a therapeutic agent.

An implantable device can be fabricated with a coating containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

As used herein, a material that is described as a layer or a film (e.g., a coating) "disposed over" an indicated substrate (e.g., an implantable device) refers to, e.g., a coating of the material deposited directly or indirectly over at least a portion of the surface of the substrate. Direct depositing means that the coating is applied directly to the exposed surface of the substrate. Indirect depositing means that the coating is applied to an intervening layer that has been deposited directly or indirectly over the substrate. In some embodiments, the term a "layer" or a "film" excludes a film or a layer formed on a non-implantable device.

In the context of a stent, "delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

Semi-Crystalline Polymers

The semi-crystalline copolymer as described herein can have crystalline domains and amorphous domains and can be expressed as FIG. 1. Generally, whether the semi-crystalline polymer would or would not flow at a certain temperature can be assessed by an onset glass transition temperature ($T_g$), which is defined as the temperature at which the polymer starts to flow, or melting transition ($T_m$) temperature of the polymer. If a coating comprising a semi-crystalline polymer having both the $T_g$ and the $T_m$ of the semi-crystalline polymer below the given temperature (e.g., ETO sterilization or crimping temperature) is heated at the given temperature, the coating will flow, compromising coating integrity. Therefore, to prevent a coating from flowing or adhering to a balloon used with a medical device having the coating, the coating would need to have an onset $T_g$ or/and $T_m$ above the given temperature. For convenience of discussion, the given temperature is defined as the temperature of a coating treatment process ($T_t$).

To form a coating comprising a semi-crystalline polymer having an onset $T_g$ below $T_t$, the semi-crystalline polymer must have one or more crystalline domains having one or more crystalline polymer structures with a molar ratio sum of the crystalline domains (x, e.g., 10-30% crystallinity) (having $T_m$s) and one or more amorphous domains having one or more amorphous polymer structures with a molar ratio sum of the amorphous domains (y) (having glass transition temperatures, $T_y$) that meet the definition set forth by the following equation:

$$x+y=1 \quad \text{(equation 1)};$$

In some embodiments, the semi-crystalline polymer has a crystalline domain having a $T_m$ of about 60° C. or above. In these embodiments, the glass transition temperature of the amorphous domain can be lower than $T_t$.

In equation 1, x and y can each range from about 0.01 to about 0.99. Some exemplary values for x and y, independently, are, about 0.02, about 0.05, about 0.1, about 0.2, about 0.3, about 0.4, about 0.5, about 0.6, about 0.7, about 0.8, about 0.9, about 0.95, or about 0.98.

The term "$T_t$" can be the temperature of working process of any coating procedure or a treatment process at any given time point. For example, $T_t$ can be the temperature of a baking procedure, a crimping procedure, or an ETO sterilization procedure. Therefore, $T_t$ can be a temperature above the ambient temperature (e.g., above 25° C.) but below about 150° C. In some embodiments, $T_t$ can be about 50° C., about 80° C., about 100° C., or about 120° C.

In some embodiments, the semi-crystalline copolymer can be, e.g., poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(D-lactic acid-co-glycolide-co-caprolactone) (PDLA-GA-CL), poly(L-lactic acid-co-glycolide-co-caprolactone) (PLLA-GA-CL), poly(DL-lactic acid-co-glycolide-co-caprolactone) (PDLLA-GA-CL), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL) or any other semi-crystalline co-polymers made out of aliphatic polyesters. In all the polymers comprising both D-lactide and L-lactide the ratio of the two diastereomers could vary from 0-100, being for example 0.10, 0.50, 1, 5, 10, 20, 30, 40, 50, 60, 70, 80, 90, 95, 99, 99.5, 99.9 or any other ratio. It is assumed the when L-lactic acid or glycolic acid is used in naming a copolymer this is also equivalent to L-lactide and glycolide. In any of the previously mentioned polymers the D- or the L-lactide could alternatively be replaced with meso-lactide.

These semi-crystalline polymers have a molar ratio of the crystalline domains, x, and a molar ratio of the amorphous domains, y, as defined above, and can be random in structure or have a more block structure, or have the design of a true block copolymer. The block copolymer could be di-block, tri-block, tetra-block or penta-block co-polymers.

In some embodiments, the semi-crystalline copolymer can be a semi-crystalline terpolymer. Such terpolymer includes repeating units from three different monomers and can include one monomer or two different monomers for providing a crystalline domain and one monomer or two different monomers for providing an amorphous domain. While the specific ratio(s) of the monomers may vary, the terpolymer will have repeating units from three different monomers, and the terpolymer will have a molar ratio, x, of the crystalline domain, which can include repeating units from one or two different monomers, and a molar ratio, y, of the amorphous domain in the terpolymer, which can include repeating units from one monomer or two different monomers, as defined above. In some embodiments, the one monomer or two different monomers providing a crystalline domain to the terpolymer can be, e.g., L-lactic acid, D-lactic acid, glycolic acid, caprolactone, dioxanone. The one monomer or two different monomers providing an amorphous domain to the terpolymer can be, e.g., caprolactone, substituted caprolactone, glycolic acid, D,L-lactic acid, L-lactic acid, D-Lactic acid, meso-lactic acid, trimethylene carbonate, or substituted trimethylene carbonate.

In some embodiments, the semi-crystalline polymer can be a semi-crystalline block copolymer. Such copolymer includes repeating units one or more monomers for providing the crystalline domains (crystalline block) and one or more monomers for providing the amorphous domains (amorphous block). Where the crystalline blocks would also provide amorphous domains and further the crystalline domain or block and/or the amorphous domain or block include repeating units from one or more different monomers, such the monomers forming the crystalline domain or block, e.g., monomers A, B, C . . . , can have different molar ratio(s), independently ranging from 0 to about 100, for example, and such monomers forming the amorphous domain or block, e.g., monomers A', B', C' . . . , can have different molar ratio(s), independently ranging from 0 to about 100, for example. However, the semi-crystalline block copolymer must have a molar ratio, x, of the crystalline domain or block and a molar ratio, y, of the amorphous domain or block as defined above. In some embodiments, the monomer(s) providing a crystalline domain to the semi-crystalline block copolymer can be, e.g., L-lactic acid, D-lactic acid, glycolic acid, caprolactone, dioxanone. The monomer(s) providing an amorphous domain to the semi-crystalline block copolymer can be, e.g., caprolactone, substituted caprolactone, glycolic acid, D,L-lactic acid, L-lactic acid, D-Lactic acid, meso-lactic acid, trimethylene carbonate, or substituted trimethylene carbonate, poly(ethylene glycol) (PEG), polypropylene oxide) (PPO), amides, or any other bioabsorbable segment.

In some embodiments, the semi-crystalline polymer can be a semi-crystalline poly(ester amide) (PEA). Such a PEA polymer can include a crystalline domain and an amorphous domain. The crystalline domain and the amorphous domain each have a molar ratio, x and y, as defined above. Some examples of semi-crystalline PEA polymers include, but are not limited to, those comprising L-phenyl alanine, D-phenyl alanine, or other units that would make a polymer crystallize such as long aliphatic chains or aromatic groups.

In some further embodiments, the semi-crystalline polymer can be any of the following polymers:

semi-crystalline PLLGA with content of L-lactide ranging from about 65 molar % to about 100 molar %;

semi-crystalline PLLA-GA-CL terpolymer with content of L-lactide ranging from about 65 molar % or higher; and semi-crystalline PLLA-CL (L-lactide/CL=75/25 or 70/30 by molar).

The molecular weights of the above polymers can vary. In some embodiments, the weight average molecular weight (Mw) of these polymers can range from about 75K Daltons to about 250K Daltons. In some embodiments, the Mw of these polymers range from about 100K Daltons to about 200K Daltons.

In some embodiments, the term "crystalline domain(s)" or "amorphous domain(s)" can be referred to as "crystalline unit(s)" or "amorphous unit(s)." In some embodiments, the term "repeating unit(s)" can also be referred to as "crystalline unit(s)" or "amorphous unit(s)."

Amorphous Polymers

The amorphous primer layer can be formed of any one or more amorphous polymer(s). In some embodiments, the amorphous polymer is an amorphous polyester polymer. Some examples of amorphous polyesters include, but are not limited to:

amorphous poly(D,L-lactide) (PDLA);

amorphous poly(L-lactide-co-D,L-lactide) (PLLLA) with D,L-lactide content of about 30 molar % or above;

amorphous poly(D,L-lactide-co-glycolide) (PDLGA) with glycolide content of about 10 to about 50 molar %;

amorphous poly(L-lactide-co-glycolide) (PLLGA) with L-lactide content of about 70 molar % or below;

amorphous poly(glycolide-co-caprolactone) (PGACL) with glycolide content of about 70 molar % or below;

amorphous poly(D,L-lactide-co-caprolactone) (PDLACL) with caprolactone content of about 70 molar % or below;

amorphous poly(L-lactide-co-caprolactone) (PLLACL) with L-lactide content of below 70 molar % but above 30 molar %;

amorphous copolymers of trimethylene carbonate with glycolide, D,L-lactide, and/or L-lactide; and amorphous PDLGA-CL and PLLA-GA-CL terpolymers with content of L-lactide of about 65 molar % or below.

The amorphous polymers can have different molecular weights. In some embodiments, the amorphous polymers listed above can have a weight average molecular weight (Mw) between about 75K Daltons to about 200K Daltons.

The primer polymer can be selected to degrade more slowly than the reservoir layer. In some embodiments, it can be selected to degrade or absorb faster than the reservoir layer. In some embodiments, the primer layer can degrade or absorb completely or substantially completely within about 6 months after deployment.

In some embodiments, the amorphous polymer can be subjected to degradation modulation to bring the overall coating degradation or absorption rate within a desired range. One example of such modulating the degradation or absorption rate of the amorphous polymer is to subject the polymer to E-beam or gamma irradiation treatment, which is a procedure well known in the art.

As used herein, the term "substantially completely" shall mean about 20% or less than 20% by weight of polymer residue remains. In some embodiments, the term shall mean less than about 10% by weight of polymer residue remains. In some further embodiments, the term shall mean less than 5% or 1% by weight of polymer residue remains.

Biologically Active Agents

In some embodiments, the implantable device described herein can optionally include at least one biologically active ("bioactive") agent. The at least one bioactive agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In certain embodiments, optionally in combination with one or more other embodiments described herein, the implantable device can include at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), deforolimus, temsirolimus, prodrugs thereof, co-drugs thereof, and combinations thereof. An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent can be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX™ (bivalirudin, from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.,* 70A:10-19 (2004). Endothelial cells can be selectively targeted (for the targeted delivery of immunoliposomes) using scFv A5. T. Volkel, et al., *Biochimica et Biophysica Acta,* 1663:158-166 (2004). Junction membrane protein vascular endothelial (VE)-cadherin has been shown to bind to endothelial cells and down regulate apoptosis of the endothelial cells. R. Spagnuolo, et al., *Blood,* 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Tyr-Gly). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the implantable device of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), temsirolimus, deforolimus, pimecrolimus, imatinib mesylate, midostaurin, clobetasol, progenitor cell-capturing antibodies, prohealing drugs, prodrugs thereof, co-drugs thereof, and a combination thereof. In a particular embodiment, the bioactive agent is everolimus. In another specific embodiment, the bioactive agent is clobetasol.

An alternative class of drugs would be p-para-α-agonists for increased lipid transportation, examples include fenofibrate.

In some embodiments, optionally in combination with one or more other embodiments described herein, the at least one biologically active agent specifically cannot be one or more of any of the bioactive drugs or agents described herein.

Coating Construct

According to some embodiments of the invention, optionally in combination with one or more other embodiments described herein, a coating disposed over an implantable device (e.g., a stent) can include a semi-crystalline polymer in the reservoir layer and an amorphous polymer in the primer layer described herein in a layer according to any design of a coating. The coating can be a multi-layer structure that includes at least one primer layer, which is layer (1) described below, and at least one reservoir layer, which is layer (2) described below, and can include any of the following (3), (4) and (5) layers or combination thereof:

(1) a primer layer;
(2) a reservoir layer (also referred to "matrix layer" or "drug matrix"), which can be a drug-polymer layer including at least one polymer (drug-polymer layer) or, alternatively, a polymer-free drug layer;
(3) a release control layer (also referred to as a "rate-limiting layer");
(4) a topcoat layer; and/or
(5) a finishing coat layer.

In some embodiments, a coating of the invention can include two or more reservoir layers described above, each of which can include a bioactive agent described herein.

Each layer of a coating can be disposed over the implantable device (e.g., a stent) by dissolving the semi-crystalline polymer, optionally with one or more other polymers, in a solvent, or a mixture of solvents, and disposing the resulting coating solution over the stent by spraying or immersing the stent in the solution. After the solution has been disposed over the stent, the coating is dried by allowing the solvent to evaporate. The process of drying can be accelerated if the drying is conducted at an elevated temperature. The complete stent coating can be optionally annealed at a temperature between about 40° C. and about 150° C. for a period of time between about 5 minutes and about 60 minutes, if desired, to allow for crystallization of the polymer coating, and/or to improve the thermodynamic stability of the coating.

To incorporate a bioactive agent (e.g., a drug) into the reservoir layer, the drug can be combined with the polymer solution that is disposed over the implantable device as described above. Alternatively, if it is desirable a polymer-free reservoir can be made. To fabricate a polymer-free reservoir, the drug can be dissolved in a suitable solvent or mixture of solvents, and the resulting drug solution can be disposed over the implantable device (e.g., stent) by spraying or immersing the stent in the drug-containing solution.

Instead of introducing a drug via a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. Optionally, a surfactant can be added to stabilize the suspension. The suspension can be mixed with a polymer solution and the mixture can be disposed over the stent as described above. Alternatively, the drug suspension can be disposed over the stent without being mixed with the polymer solution.

The drug-polymer layer can be applied indirectly over at least a portion of the stent surface to serve as a reservoir for at least one bioactive agent (e.g., drug) that is incorporated into the reservoir layer over at least a portion of the primer layer. The primer layer can be applied between the stent and the reservoir to improve the adhesion of the drug-polymer layer to the stent. The optional topcoat layer can be applied over at least a portion of the reservoir layer and serves as a rate-limiting membrane that helps to control the rate of release of the drug. In one embodiment, the topcoat layer can be essentially free from any bioactive agents or drugs. If the topcoat layer is used, the optional finishing coat layer can be applied over at least a portion of the topcoat layer for further control of the drug-release rate and for improving the biocompatibility of the coating. Without the topcoat layer, the finishing coat layer can be deposited directly on the reservoir layer.

Sterilization of a coated medical device generally involves a process for inactivation of micropathogens. Such processes are well known in the art. A few examples are e-beam, ETO sterilization, autoclaving, and gamma irradiation. Most, if not all, of these processes can involve an elevated temperature. For example, ETO sterilization of a coated stent generally involves heating above 50° C. at humidity levels reaching up to 100% for periods of a few hours up to 24 hours. A typical EtO cycle would have the temperature in the enclosed chamber to reach as high as above 50° C. within the first 3-4 hours then and fluctuate between 40° C. to 50° C. for 17-18 hours while the humidity would reach the peak at 100% and maintain above 80% during the fluctuation time of the cycle.

The process of the release of a drug from a coating having both topcoat and finishing coat layers includes at least three steps. First, the drug is absorbed by the polymer of the topcoat layer at the drug-polymer layer/topcoat layer interface. Next, the drug diffuses through the topcoat layer using the void volume between the macromolecules of the topcoat layer polymer as pathways for migration. Next, the drug arrives at the topcoat layer/finishing layer interface. Finally, the drug diffuses through the finishing coat layer in a similar fashion, arrives at the outer surface of the finishing coat layer, and desorbs from the outer surface. At this point, the drug is released into the blood vessel or surrounding tissue. Consequently, a combination of the topcoat and finishing coat layers, if used, can serve as a rate-limiting barrier. The drug can be released by virtue of the degradation, dissolution, and/or erosion of the layer(s) forming the coating, or via migration of the drug through the semi-crystalline polymeric layer(s) into a blood vessel or tissue.

In one embodiment, except for the primer layer, any or all of other layers of the stent coating can be made of a semi-crystalline polymer described herein, optionally having the properties of being biologically degradable/erodable/absorbable/resorbable, non-degradable/biostable polymer, or a combination thereof.

In another embodiment, except for the reservoir layer, any or all of other layers of the stent coating can be made of an amorphous polymer described herein, optionally having the properties of being biologically degradable/erodable/absorbable/resorbable, non-degradable/biostable polymer, or a combination thereof.

If a finishing coat layer is not used, the topcoat layer can be the outermost layer and can be made of a semi-crystalline polymer and/or an amorphous polymer described herein and optionally having the properties of being biodegradable or, biostable, or being mixed with an amorphous polymer. In this case, the remaining layers (i.e., the primer and the reservoir layer) optionally can also be fabricated of a semi-crystalline polymer described herein and optionally having the properties of being biodegradable or, biostable, or being mixed with an amorphous polymer The polymer(s) in a particular layer may be the same as or different than those in any of the other layers, as long as the outside of another bioabsorbable should preferably also be bioabsorbable and degrade at a similar or faster relative to the inner layer.

If neither a finishing coat layer nor a topcoat layer is used, the stent coating could have only two layers—the primer and the reservoir. In such a case, the reservoir is the outermost layer of the stent coating and should be made of a semi-crystalline polymer described herein and optionally having the properties of being biodegradable or, biostable, or being mixed with an amorphous polymer. The primer layer is fabricated of an amorphous polymer described herein and optionally one or more biodegradable polymer(s), biostable polymer(s), or a combination thereof.

Any layer of a coating, except for the primer layer, can contain any amount of a semi-crystalline polymer described herein and optionally having the properties of being biodegradable or, biostable. Non-limiting examples of bioabsorbable polymers and biocompatible polymers include poly(N-vinyl pyrrolidone); polydioxanone; polyorthoesters; polyanhydrides; poly(glycolic acid); poly(glycolic acid-co-trimethylene carbonate); polyphosphoesters; polyphosphoester urethanes; poly(amino acids); poly(trimethylene carbonate); poly(iminocarbonates); co-poly(ether-esters); polyalkylene oxalates; polyphosphazenes; biomolecules, e.g., fibrin, fibrinogen, cellulose, cellophane, starch, collagen, hyaluronic acid, and derivatives thereof (e.g., cellulose acetate, cellulose butyrate, cellulose acetate butyrate, cellulose nitrate, cellulose propionate, cellulose ethers, and carboxymethyl cellulose), polyurethane, polyesters, polycarbonates, polyurethanes, poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(D-lactic acid-co-glycolide-co-caprolactone) (PDLA-GA-CL), poly(L-lactic acid-co-glycolide-co-caprolactone) (PLLA-GA-CL), poly(DL-lactic acid-co-glycolide-co-caprolactone) (PDLLA-GA-CL), poly (L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), or any copolymers thereof.

Any layer of a stent coating can also contain any amount of a non-degradable polymer, or a blend of more than one such polymer as long as it is not mixed with a bioabsorbable polymer or any layer underneath the non-degradable layer comprise a bioabsorbable polymer. Non-limiting examples of non-degradable polymers include poly(methylmethacrylate), poly(ethylmethacrylate), poly(butylmethacrylate), poly(2-ethylhexylmethacrylate), poly(laurylmethacrylate), poly(2-hydroxyethyl methacrylate), polyethylene glycol (PEG) acrylate, PEG methacrylate, 2-methacryloyloxyethylphosphorylcholine (MPC) and poly(n-vinyl pyrrolidone), poly(methacrylic acid), poly(acrylic acid), poly(hydroxypropyl methacrylate), poly(hydroxypropylmethacrylamide), poly(3-trimethylsilylpropyl methacrylate), and copolymers thereof.

Method of Fabricating Implantable Device

Other embodiments of the invention, optionally in combination with one or more other embodiments described herein, are drawn to a method of fabricating an implantable device. In one embodiment, the method comprises forming the implantable device of a material containing a biodegradable or biostable polymer or copolymer.

Under the method, a portion of the implantable device or the whole device itself can be formed of the material containing a biodegradable or biostable polymer or copolymer. The method can deposit a coating having a range of thickness over an implantable device. In certain embodiments, the method deposits over at least a portion of the implantable device a coating that has a thickness of ≤about 30 microns, or ≤about 20 microns, or ≤about 10 microns, or ≤about 5 microns.

In certain embodiments, the method is used to fabricate an implantable device selected from stents, grafts, stent-grafts, catheters, leads and electrodes, clips, shunts, closure devices, valves, and particles. In a specific embodiment, the method is used to fabricate a stent.

In some embodiments, to form an implantable device formed from a polymer, a polymer or copolymer optionally including at least one bioactive agent described herein can be formed into a polymer construct, such as a tube or sheet that can be rolled or bonded to form a construct such as a tube. An implantable device can then be fabricated from the construct. For example, a stent can be fabricated from a tube by laser machining a pattern into the tube. In another embodiment, a polymer construct can be formed from the polymeric material of the invention using an injection-molding apparatus.

Non-limiting examples of polymers, which may or may not be the semi-crystalline polymers defined above, that can be used to fabricate an implantable device include poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(D-lactic acid-co-glycolide-co-caprolactone) (PDLA-GA-CL), poly(L-lactic acid-co-glycolide-co-caprolactone) (PLLA-GA-CL), poly(DL-lactic acid-co-glycolide-co-caprolactone) (PDLLA-GA-CL), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), poly(thioesters), poly(trimethylene carbonate), polyethylene amide, polyethylene acrylate, poly(glycolic acid-co-trimethylene carbonate), co-poly(ether-esters) (e.g., PEO/PLA), polyphosphazenes, biomolecules (e.g., fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (e.g., polyvinyl chloride), polyvinyl ethers (e.g., polyvinyl methyl ether), polyvinylidene halides (e.g., polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, rayon, rayon-triacetate, cellulose and derivates thereof (e.g., cellulose acetate, cellulose butyrate, cellulose acetate butyrate, cellophane, cellulose nitrate, cellulose propionate, cellulose ethers, and carboxymethyl cellulose), and copolymers thereof.

Additional representative examples of polymers that may be suited for fabricating an implantable device include ethylene vinyl alcohol copolymer (commonly known by the generic name EVOH or by the trade name EVAL®), poly(butyl methacrylate), poly(vinylidene fluoride-co-hexafluoropropylene) (e.g., SOLEF® 21508, available from Solvay Solexis PVDF of Thorofare, N.J.), polyvinylidene fluoride (otherwise known as KYNAR®, available from Atofina Chemicals of Philadelphia, Pa.), poly(tetrafluoroethylene-co-hexafluoropropylene-co-vinylidene fluoride), ethylene-vinyl acetate copolymers, and polyethylene glycol.

Method of Treating or Preventing Disorders

An implantable device according to the present invention can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. A portion of the implantable device or the whole device itself can be formed of the material, as described herein. For example, the material can be a coating disposed over at least a portion of the device.

In certain embodiments, optionally in combination with one or more other embodiments described herein, the inventive method treats, prevents or diagnoses a condition or disorder selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In a particular embodiment, the condition or disorder is atherosclerosis, thrombosis, restenosis or vulnerable plaque.

In one embodiment of the method, optionally in combination with one or more other embodiments described herein, the implantable device is formed of a material or includes a coating containing at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), temsirolimus, deforolimus, pimecrolimus, imatinib mesylate, midostaurin, clobetasol, progenitor cell-capturing antibodies, prohealing drugs, fenofibrate, prodrugs thereof, co-drugs thereof, and a combination thereof.

In certain embodiments, optionally in combination with one or more other embodiments described herein, the implantable device used in the method is selected from stents, grafts, stent-grafts, catheters, leads and electrodes, clips, shunts, closure devices, valves, and particles. In a specific embodiment, the implantable device is a stent.

EXAMPLES

The following non-limiting examples illustrate the various embodiments described above.

Figure 3:
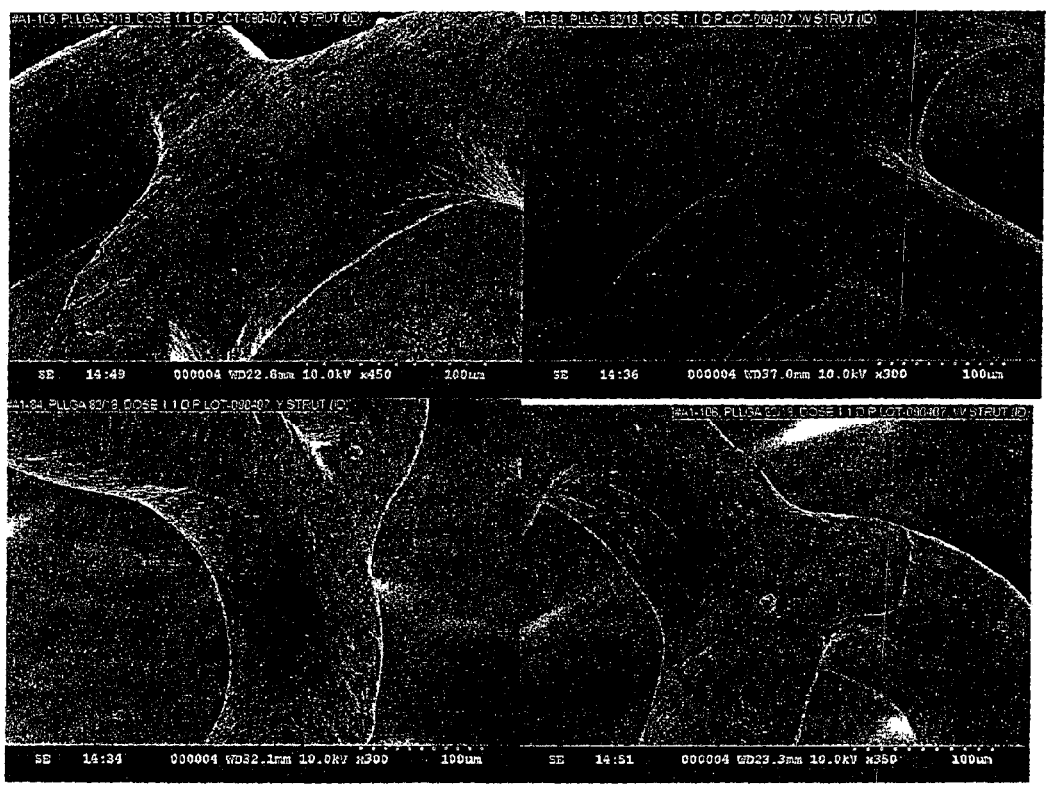
FIG. 3 shows scanning electron micrograph (SEM) images of coating integrity after simulated use for semicrystalline PLLGA (82/18) as drug reservoir and amorphous PLLGA (75/25) as primer layer.

A PLLA-GA (L-lactide-co-glycolide, 82/18, molar ratio) polymer and everolimus were coated onto stents (drug/polymer=1/3) using a solvent mixture of acetone/MIBK (methyl isobutyl ketone) (90/10 w/w). The coated stents were then crimped onto a balloon catheter and sterilized by ETO. The coating integrity was evaluated following a simulated use test. FIGS. 2A-2D show scanning electron microscope (SEM) images of an ETO sterilized coating made from semi-crystalline PLLA-GA (L-lactide-co-glycolide, 82/18 molar ratio) after simulated use test, which shows the superior integrity of the coating when compared to a coating made from amorphous poly(D,L-lactide-co-glycolide) (PDLGA) (lactide/glycolide, 75/25, molar ratio), the SEM images of which are shown in FIG. 3. The semi-crystalline coating shows little, if any, coating softening and minor balloon adhesion (FIGS. 2A-2D) while the amorphous coating shows more severe coating softening and as a result change of shape around the balloon (FIG. 3).

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention.

The invention claimed is:

1. An implantable device, comprising a coating comprising:
a reservoir layer comprising a biodegradable semi-crystalline polymer and a bioactive agent,
and
a primer comprising a biodegradable amorphous polymer;
wherein the semi-crystalline polymer is selected from the group consisting of semi-crystalline poly(L-lactide-co-glycolide) (PLLA-GA) polymers with the content of L-lactide ranging from about 65 molar % to about 100 molar %, semi-crystalline poly(L-lactide-co-caprolactone) (PLLA-CL) (L-lactide/CL=75/25 by molar) polymer, semi-crystalline poly(L-lactide-co-caprolactone) (PLLA-CL) (L-lactide/CL=70/30 by molar) polymer, and combinations thereof;
wherein the amorphous polymer has a miscibility of at least 5% in the semi-crystalline polymer;
wherein the amorphous polymer comprises a polyester having a degradation rate faster than the semi-crystalline polymer;
and
wherein the coating has a degradation or absorption rate that within a period of 6 months after deployment of the implantable device, the coating has a mass loss of about 80% or more.

2. The implantable device of claim 1, wherein the bioactive agent is selected from the group consisting of paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), biolimus, tacrolimus, dexamethasone, rapamycin, 40-O-(2-hydroxyethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), temsirolimus, deforolimus, γ-hiridun, clobetasol, pimecrolimus, imatinib mesylate, midostaurin, feno fibrate, and combinations thereof.

3. The implantable device of claim 1, wherein the amorphous polymer has a glass-transition temperature ($T_g$) higher than the semi-crystalline polymer.

4. The implantable device of claim 1, wherein the semi-crystalline polymer is a semi-crystalline PLLA-GA polymer with the content of L-lactide ranging from about 65 molar % to about 100 molar %.

5. The implantable device of claim 1, wherein the semi-crystalline polymer is semi-crystalline PLLA-CL (L-lactide/CL=75/25 or 70/30 by molar).

6. The implantable device of claim 1, wherein the amorphous polymer is selected from the group consisting of amorphous poly(D,L-lactide) (PDLA), amorphous poly(L-lactide-co-D,L-lactide) (PLLLA) with D,L-lactide content of about 30 molar % or above, amorphous poly(D,L-lactide-co-glycolide) (PDLGA) with glycolide content of about 10 to about 50 molar %, amorphous poly(L-lactide-co-glycolide) (PLLGA) with L-lactide content of about 75 molar % or below, amorphous poly(glycolide-co-caprolactone) (PGACL) with glycolide content of about 70 molar % or below, amorphous poly(D,L-lactide-co-caprolactone) (PDLACL) with caprolactone content of about 70 molar % or below, amorphous poly(L-lactide-co-caprolactone) (PLLACL) with L-lactide content of below 70 molar % but above 30 molar %, amorphous copolymers of trimethylene carbonate with glycolide, D,L-lactide, and/or L-lactide, amorphous PDLGA-CL and PLLA-GA-CL terpolymers with content of L-lactide of about 65 molar % or below, and combinations thereof.

7. The implantable device of claim 1, wherein the amorphous polymer is subjected to E-beam or gamma irradiation treatment to enhance its degradation rate prior to its use in forming the primer layer.

8. The implantable device of claim 1, wherein the amorphous polymer is selected from the group consisting of amorphous poly(D,L-lactide-co-glycolide) (PDLGA) with glycolide content of about 10 to about 50 molar %, amorphous poly(L-lactide-co-glycolide) (PLLGA) with L-lactide content of about 75 molar % or below, amorphous poly(glycolide-co-caprolactone) (PGACL) with glycolide content of about 70 molar % or below, amorphous copolymers of trimethylene carbonate with glycolide, amorphous copolymers of trimethylene carbonate with glycolide and D,L-lactide, amorphous copolymers of trimethylene carbonate with glycolide and L-lactide, amorphous PDLGA-CL and PLLA-GA-CL terpolymers with content of L-lactide of about 65 molar % or below, and combinations thereof.

9. The implantable device of claim 1, wherein the bioactive agent is selected from the group consisting of paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), temsirolimus, deforolimus, γ-hiridun, clobetasol, pimecrolimus, imatinib mesylate, midostaurin, feno fibrate, prodrugs thereof, co-drugs thereof, and combinations thereof.

10. The implantable device of claim 1, which is a stent.

11. The implantable device of claim 8, which is a stent.

12. A method of fabricating an implantable device, comprising
forming a coating comprising a semi-crystalline reservoir layer that comprises a biodegradable semi-crystalline polymer and a bioactive agent, and an amorphous primer layer that comprises a biodegradable amorphous polymer;
wherein the semi-crystalline polymer is selected from the group consisting of semi-crystalline poly(L-lactide-co-glycolide) (PLLA-GA) polymers with the content of L-lactide ranging from about 65 molar % to about 100 molar %, semi-crystalline poly(L-lactide-co-caprolactone) (PLLA-CL) (L-lactide/CL=75/25 by molar) polymer, semi-crystalline poly(L-lactide-co-caprolactone) (PLLA-CL) (L-lactide/CL=70/30 by molar) polymer, and combinations thereof;
wherein the amorphous polymer has a miscibility of at least 5% in the semi-crystalline polymer;
wherein the amorphous polymer comprises a polyester having a degradation rate faster than the semi-crystalline polymer;
and
wherein the coating has a degradation or absorption rate that within a period of 6 months after deployment of the implantable device, the coating has a mass loss of about 80% or more.

13. The method of claim 12, wherein the bioactive agent is selected from the group consisting of paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), biolimus, tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), temsirolimus, deforolimus, γ-hiridun, clobetasol, pimecrolimus, imatinib mesylate, midostaurin, feno fibrate, and combinations thereof.

14. The method of claim 12, wherein the amorphous polymer has a glass-transition temperature $(T_g)$ higher than the semi-crystalline polymer.

15. The method of claim 12, wherein the semi-crystalline polymer is a semi-crystalline PLLA-GA polymer with the content of L-lactide ranging from about 65 molar % to about 100 molar %.

16. The method of claim 12, wherein the semi-crystalline polymer is semi-crystalline PLLA-CL (L-lactide/CL=75/25 or 70/30 by molar).

17. The method of claim 12, wherein the amorphous polymer is selected from the group consisting of amorphous poly(D,L-lactide) (PDLA), amorphous poly(L-lactide-co-D,L-lactide) (PLLLA) with D,L-lactide content of about 30 molar % or above, amorphous poly(D,L-lactide-co-glycolide) (PDLGA) with glycolide content of about 10 to about 50 molar %, amorphous poly(L-lactide-co-glycolide) (PLLGA) with L-lactide content of about 75 molar % or below, amorphous poly(glycolide-co-caprolactone) (PGACL) with glycolide content of about 70 molar % or below, amorphous poly(D,L-lactide-co-caprolactone) (PDLACL) with caprolactone content of about 70 molar % or below, amorphous poly(L-lactide-co-caprolactone) (PLLACL) with L-lactide content of below 70 molar % but above 30 molar %, amorphous copolymers of trimethylene carbonate with glycolide, D,L-lactide, and/or L-lactide, amorphous PDLGA-CL and PLLA-GA-CL terpolymers with content of L-lactide of about 65 molar % or below, and combinations thereof.

18. The method of claim 12, wherein the amorphous polymer is subjected to E-beam or gamma irradiation treatment to enhance its degradation rate prior to its use in forming the primer layer.

19. The method of claim 12, wherein the amorphous polymer is selected from the group consisting of amorphous poly(D,L-lactide-co-glycolide) (PDLGA) with glycolide content of about 10 to about 50 molar %, amorphous poly(L-lactide-co-glycolide) (PLLGA) with L-lactide content of about 75 molar % or below, amorphous poly(glycolide-co-caprolactone) (PGACL) with glycolide content of about 70 molar % or below, amorphous copolymers of trimethylene carbonate with glycolide, amorphous copolymers of trimethylene carbonate with glycolide and D,L-lactide, amorphous copolymers of trimethylene carbonate with glycolide and L-lactide, amorphous PDLGA-CL and PLLA-GA-CL terpolymers with content of L-lactide of about 65 molar % or below, and combinations thereof.

20. The method of claim 12, wherein the bioactive agent is selected from the group consisting of paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), temsirolimus, deforolimus, γ-hiridun, clobetasol, pimecrolimus, imatinib mesylate, midostaurin, feno fibrate, prodrugs thereof, co-drugs thereof, and combinations thereof.

* * * * *